United States Patent [19]

Sheehan

[11] Patent Number: 4,795,631

[45] Date of Patent: Jan. 3, 1989

[54] WATER BASED LIP COLOR COMPRISING AN ALKALI SOLUBLE FILM-FORMING AGENT

[75] Inventor: Kathleen Sheehan, Branford, Conn.

[73] Assignee: Chesebrough-Pond's, Inc., Greenwich, Conn.

[21] Appl. No.: 844,474

[22] Filed: Mar. 26, 1986

[51] Int. Cl.$^4$ .............................................. A61K 7/025
[52] U.S. Cl. .......................................... 424/64; 424/81
[58] Field of Search ...................... 424/63, 64, 81, 401

[56] References Cited

U.S. PATENT DOCUMENTS

| | | | |
|---|---|---|---|
| 2,230,063 | 1/1939 | Klimist | 424/64 |
| 2,548,970 | 10/1948 | Grate | 424/64 |
| 3,007,887 | 11/1961 | Essig | 524/831 |
| 3,088,876 | 5/1963 | Buth | 424/64 |
| 3,122,481 | 2/1964 | Wotzelka et al. | 424/64 |
| 3,590,118 | 6/1971 | Conrady | 424/405 |
| 3,911,105 | 10/1975 | Papantoniou et al. | 424/64 |
| 3,927,203 | 12/1975 | Seymour et al. | 424/61 |
| 3,937,811 | 2/1976 | Papantoniou et al. | 424/63 |
| 3,957,969 | 5/1976 | Fujiyama et al. | 424/64 |
| 3,981,987 | 8/1976 | Linke et al. | 424/47 |
| 4,423,031 | 12/1983 | Murui et al. | 424/63 |
| 4,529,773 | 7/1985 | Witiak et al. | 524/558 |
| 4,552,755 | 11/1985 | Randen | 424/81 |
| 4,699,780 | 10/1987 | Jennings et al. | 424/60 |

FOREIGN PATENT DOCUMENTS 0752558 12/1970 Belgium .

OTHER PUBLICATIONS

"Carboset Resins"–1984.
"Cosmetics with Carboset Resins"–1981.
Poucher, "Perfumes, Cosmetics and Soaps" 8th edition–Chapter 8 (1974).
"Harrys Cosmeticology"–Chapter 19.
Balsam & Sagarin "Cosmetics: Science and Technology"–Chapter 12 (1972).
de Navarre "The Chemistry and Manufacture of Cosmetics"–Chapter 44 (1975).

*Primary Examiner*—John E. Kittle
*Assistant Examiner*—Susan S. Rucker
*Attorney, Agent, or Firm*—Brumbaugh, Graves, Donohue & Raymond

[57] ABSTRACT

Flexible, long-wearing, water-resistant lip-films are formed from water-based compositions comprising water; an alkali-dispersible or alkali soluble, water-insoluble thermoplastic film forming resin; a volatile base; and a water-insoluble plasticizer.

7 Claims, No Drawings

WATER BASED LIP COLOR COMPRISING AN ALKALI SOLUBLE FILM-FORMING AGENT

BACKGROUND OF THE INVENTION

The present invention relates to a lip-film formulation which provides a thin, flexible, water-resistant film when applied to the lips and allowed to dry. The lip-film thus formed is long-wearing and does not smear or bleed.

Commercial lip color is generally supplied as either a lipstick or a lip gloss. Lipsticks are blends of waxes, oils, and colorants which are mixed together and then melted and molded to form a stick. Lip gloss is a semi-solid mixture of wax, oils, and colorants containing relatively less wax than a lipstick formulation.

When applied, both lipstick and lip gloss remain in a semi-solid state. This results in the need for frequent reapplication to maintain the desired cosmetic effect, as the lipstick or gloss is worn off in the course of eating, drinking, smoking, or just talking. Lipstick and lip gloss are also prone to smearing, and can cause hard to remove stains on clothing.

Lip films have been described in the literature, but they either do not address the above problems, or have other disadvantages of their own. U.S. Pat. No. 2,230,063 describes a lip film composition in which ethyl cellulose was used as a film former in an ethanolic solution. This led to a moisture-proof, smear-proof film, but the application of ethanol to the lips was found to be unacceptably irritating and drying.

U.S. Pat. No. 3,122,481 used methyl cellulose to form a lip-film based on an aqueous solvent. This addressed the difficulties posed by the ethanol of U.S. Pat. No. 2,230,063, but did not produce a water resistant film. Methyl cellulose is readily water soluble and, therefore, the resulting films did not wear well, since they were rapidly dissolved when contacted with aqueous liquids, e.g., saliva or beverages.

Other patents also describe lip-film formulations. U.S. Pat. No. 2,548,970 makes use of gum benzoin and cetyl alcohol to form a lip film. U.S. Pat. No. 3,088,876 teaches lipsticks in which film forming rosin or rosin derivatives and wax are dissolved in a solvent. Both of these patents rely on alcohol or other organic solvents, however, and therefore have problems with drying and irritation.

Film-forming acrylate resins are known which produce films which are water-resistant, yet which are soluble in basic aqueous solution. U.S. Pat. No. 3,590,118 teaches the use of such a resin as a film-forming carrier for insect repellant. These resins have also been proposed for use in a variety of cosmetic applications such as body paint and eyeliner. They have not been used, however, in lip-coloring formulations which require an unusually high degree of plasticity due the extremely high mobility and irregular surface contours of the lips. Formulations for other cosmetic applications are generally unsuitable for lip-coloring applications and would tend to crack and peel as the lips move.

It is the object of this invention to provide a water-based lip-film composition which provides a comfortable, long-wearing, water-resistant film for use in applying colorants or medication to the lips.

BRIEF DESCRIPTION OF THE INVENTION

A lip film composition suitable for applying cosmetic or therapeutic agents to the lips comprises:
 (a) water;
 (b) an alkali-dispersible, water-insoluble, thermoplastic, film-forming resin;
 (c) a volatile base in sufficient quantity to solubilize the film-forming resin; and
 (d) a water-insoluble plasticizer. The film-forming resin is preferably alkali-soluble, the formation of a stable dispersion being a minimum condition. The foregoing composition results in a flexible, long-wearing, water-resistant film when applied to the lips and allowed to dry. Colorants, emollients, soothing agents, medications, sunscreens, and other ingredients may be included based on the desired end use of the composition.

DETAILED DESCRIPTION OF THE INVENTION

Lip-films according to the present inventions are formed using film-forming resins which are soluble or at least dispersable in basic aqueous solution, but insoluble in neutral or slightly acidic water. A volatile base is used to solubilize or disperse the film-forming resin in an aqueous solution. After application to the lips, both the water and the volatile base evaporate, leaving a dry, water-resistant film.

Suitable resins for use in the lip-film according to this invention are alkali-dispersible or alkali-soluble, water-insoluble, thermoplastic, film-forming resins. Particularly suitable are copolymers of acrylic acid, methacrylic acid, acrylamides, and acrylate or methacrylate esters, including terpolymers of acrylic acid, methacrylic acid and acrylamide. Sufficient acid residues should be incorporated in the polymer to allow the formation of a stable polymer dispersion in aqueous alkali, or to render the polymer soluble in aqueous alkali.

The resins used may be of essentially any molecular weight, although the size of the polymer will affect the amount of polymer used in a formulation. High molecular weight polymers have higher specific viscosities and if present in too great a quantity may lead to compositions which are difficult to apply. In general, liquid lip-film compositions should be formulated to have a viscosity of 5 to 95 Brookfield units (spindle 4; 6 rpm) and will contain from about 3% to about 30% resin.

Film-forming resins are dissolved in aqueous solutions of a volatile base. Suitable bases include ammonium hydroxide and morpholine, although any base which will evaporate from the lips and which is suitable for application to the lips both aesthetically and pharmaceutically can be used. Aesthetically suitable materials are those which are not offensive to the visual, or organoleptic senses. While triethylamine, triethanolamine, ethylenediamine, 2methylpiperazine, dibutylamine, aminomethylpropane, and aminomethylpropanediol, can also be used as a base they are not sufficiently volatile to produce a water-insoluble lip film if used alone to achieve a resin-solubilizing pH.

The base should be added in sufficient quantity to neutralize the acid residues of the resin and make the final pH of the composition basic. The final pH of the formulation should be greater than 7, and preferably 7.5–8. However, too high a pH is unsuitable as it can lead to irritation and drying of the lips.

In addition to the above ingredients, the lip-film composition according to this invention also contains a plasticizer. Since lips have irregular surface contours and are highly mobile, extreme film-flexibility is required in order to enable a film to conform to lip surfaces. Water-soluble plasticizers were found to be unsuitable for use in the lip-films of the present invention due to the fact that the levels of plasticizer which were necessary to render the film sufficiently flexible also reduced the water-resistance of the film to unacceptable levels. Accordingly, the lip-films of the present invention contain water-insoluble plasticizers which render the film flexible without reducing its water-resistance.

Suitable water-insoluble plasticizers include simple esters of $C_3$–$C_{18}$ saturated acids with $C_3$–$C_{16}$ alcohols; simple esters of $C_{18}$ unsaturated acids with $C_3$–$C_{10}$ alcohols; diesters of $C_4$–$C_{36}$ saturated diacids with $C_3$–$C_{16}$ alcohols; glycerides of $C_{12}$–$C_{22}$ fatty acids; hydrocarbons; hydrocarbon polymers; polyvinylpyrrolidone/hydrocarbon copolymers; and fatty alcohol ethers of hydrocarbon polymers.

Specific examples for each of the foregoing groups are setforth below:

Esters: Myristal Propionate, Cetyl Palmitate, Cetyl Octanoate, Ceteraryl Palmitate, Cetearyl Octanoate, Butyl Stearate, Stearyl Heptanoate, Isopropyl Stearate, Isopropyl Myristate, Octyl Stearate, Butyl Myristate, Isocetyl Stearate, Myristyl Myristate, Isopropyl Isostearate, Octyl Palmitate, Stearyl Stearate, Isopropyl Palmitate, Isopropyl Linoleate, Isodecyl Oleate, Oleyl Oleate, Decyl Oleate, Dioctyl Succinate, Diisocetyl Adipate, Diisopropyl Adipate, Diisopropyl Dimerate, Dioctyl Adipate Glycerides: Capric/Caprylic Triglyceride, Natural Oils (i.e., Mink, Vegetable, Castor)

Hydrocarbons: Petroleum Jelly, Mineral Oil

Hydrocarbon Polymers: Polybutene

PVP/Hydrocarbon Copolymers: PVP/Eicosene Copolymer, PVP/Hexadecene Copolymer

Ethers: Polyethylene Glycol ethers of fatty alcohols and of Glycerin Polypropylene Glycol ethers of fatty alcohols. Suitable Fatty Alcohols: Cetyl, Stearyl, Oleyl, Myristal, Lauryl, ethoxylation value range 2–30, propoxylation value range 10–50.

Although the alkali-soluble, water-insoluble, thermoplastic, film-forming resins of this invention have some surface activity, it may be necessary to add a small amount of a co-solvent or surfactant to keep the water-insoluble plasticizer dispersed in the liquid lip-film composition. These materials are added at levels which are low enough such that the water resistance of the film is not comprised. These materials also act as viscosity builders which assist in maintaining the dispersion.

In addition to base, film-forming resin, and plasticizer, the lip-film compositions according to the present invention may contain colorants, emollients, soothing agents, medications, sunscreens or other cosmetic or therapeutic ingredients. As will be clear to one skilled in the art, colorants for these compositions can be in the form of lakes or dyes, or other colorant materials which are approved for use in lip color formulations. Suitable colorants include: D&C Green No. 5, D&C Red No. 8, D&C Yellow No. 10, D&C Red No. 21, D&C Red No. 6, D&C Red No. 27, D&C Orange No. 5, D&C Red No. 30, D&C Green No. 3, D&C Red No. 9, D&C Yellow No. 5, D&C Red No. 33, D&C Red No. 3, D&C Red No. 36, D&C Red No. 40, D&C Yellow No. 10, D&C Blue No. 1, Annatto, Copper Powder, Bismuth Oxychloride, Guanine, Bronze Powder, Iron Oxides, Carmel, Manganese Violet, Carmine, Mica, Carotene, $TiO_2$, Chlorophyllin-Ca complex, and Zinc Oxide. Preferred colorants are lakes of D&C colors and iron oxide pigments which have been hydrophobically treated with a silicone polymer coating. Moreover, pearlescent materials may also be added to the formulations to impart a luminescent affect.

Emollients, fragrances, FDA approved sweetners and other flavorants, smoothing agents, sunscreens or medications may optionally be included in the lip-films according to this invention. Suitable materials include allantoin, p-amino benzoic acid, calamine, cocoa butter, dimethicone, glycerin, kaolin, petroleum jelly, shark liver oil, zinc acetate, zinc carbonate and zinc oxide. Preservatives may also be added to lip-film formulations. Suitable preservative compositions include:

PRESERVATIVE 1

|  | % of finished product |
| --- | --- |
| Imidazolydinyl urea (Germall 115) | 0.30% |
| methyl paraben | 0.15% |
| propyl paraben | 0.10% |

PRESERVATIVE 2

|  | % of finished product |
| --- | --- |
| Diazolidinyl Urea (Germall II) | 0.20% |
| methyl paraben | 0.15% |
| propyl paraben | 0.10% |

PRESERVATIVE 3

|  | % of finished product |
| --- | --- |
| Quaternium 15 (Dowicil 200) | 0.20% |
| methyl paraben | 0.15% |
| propyl paraben | 0.10% |

PRESERVATIVE 4

|  | % of finished product |
| --- | --- |
| phenoxyethanol | 0.70% |
| methyl paraben | 0.10% |
| ethyl paraben | 0.10% |
| butyl paraben | 0.10% |

This list of preservatives is not exhaustive, however, and it will be understood that other preservatives known in the art may also be used.

In preparing the lip-film composition according to this invention, colorant in the form of a dry powder is ground into the alkaline solution of the film-forming resin. It is necessary to achieve a fine particle size, so that colorant particles will remain suspended in the aqueous medium. This can be accomplished using a Fryma CoBall Mill or a 3 roll mill.

Alkaline solutions of film-forming resins can be prepared by adding the resin to water and base, preferably ammonium hydroxide, at 160° F. with mixing. CARBOSET 525 (260,000 MW) and CARBOSET 515 (7,000 MW) are two preferred resins available from B.F.

Goodrich. These resins dissolve readily with heating to 160° F. In the alternative, resin can be purchased already in alkaline solution such as Carboset XL-28, which is a 30% aqueous solution of a resin (40,000 MW) neutralized to pH 7.5 with ammonium hydroxide.

The pigmented resin solution is heated with mixing and any oils or waxes to be included in the formulation as plasticizers are heated to the same temperature and are added at this time. The temperature for mixing should be high enough to allow for adequate dispersion of the oils and waxes. The mixture is then allowed to cool to room temperature with vigorous mixing. Preservatives, fragrances and other heat sensitive ingredients are added during the cooling process at a temperature which is compatible with the material added.

The dry powder colorant mixtures for use in the invention are prepared by blending the desired colorant materials together under high shear conditions. A Fitz-mill or a PK Blender are suitable for preparing suitable colorant mixtures. Examples of suitable dry powder mixtures are set forth below, although it will be understood that variations in the dry powder to achieve the desired color are clearly within the scope of the present invention.

EXAMPLE I

|  | % |
| --- | --- |
| Titanium Dioxide | 50.00 |
| FD&C Red 7 Ca lake | 40.00 |
| FD&C Red 6 Ba lake | 5.00 |
| Brown Iron Oxide | 3.00 |
| Red Iron Oxide | 1.00 |
| Blue Iron Oxide | 1.00 |

EXAMPLE II

|  | % |
| --- | --- |
| Zinc Oxide | 40.00 |
| Mica | 10.00 |
| FD&C Red 7 Ca lake | 35.00 |
| Brown Iron Oxide | 5.00 |
| FD&C Blue 1 Al lake | 2.00 |
| Manganese Violet | 8.00 |

EXAMPLE III

|  | % |
| --- | --- |
| Titanium Dioxide | 15.00 |
| FD&C Red 7 Ca lake | 30.00 |
| Brown Iron Oxide | 9.00 |
| Red Iron Oxide | 5.00 |
| Blue Iron Oxide | 1.00 |
| Titanium Mica | 40.00 |

EXAMPLE IV

|  | % |
| --- | --- |
| Titanium Dioxide | 15.00 |
| Bismath Oxychloride | 20.00 |
| Titanated Mica | 25.00 |
| Brown Iron Oxide | 10.00 |
| Yellow Iron Oxide | 6.00 |
| Black Iron Oxide | 2.00 |
| FD&C Blue #1 Al lake | 2.00 |

-continued

|  | % |
| --- | --- |
| FD&C Red 7 Ca lake | 20.00 |

The foregoing formulations can be made with the ingredients surface treated with a variety of materials provided that the material is compatible with the resin solution. In particular, silicone treatment of the pigments results in a softer film and enhances water resistance.

The following formulations of the lip-film compositions of the present invention are illustrative of the disclosure hereinabove:

EXAMPLE V

|  | % |
| --- | --- |
| Water | 65.95 |
| Ammonium Hydroxide (58%) | 1.30 |
| Carboset 525 (260,000 M.W.) | 11.00 |
| Carboset 515 (7,000 M.W.) | 2.00 |
| Ethanol (SDA 40-200) | 10.00 |
| Ganex V0216 | 2.50 |
| Castor Oil | 1.00 |
| Pentaerythritol Tetra Oleate | 1.00 |
| Fragrance | .25 |
| Dry Powder & Pearl | 5.00 |

EXAMPLE VI

|  | % |
| --- | --- |
| Carboset XL-28 (30% aqueous solution of Resin, M.W. 40,000 neutralized to pH of 7.5 with NH4OH) | 75.00 |
| Dry Powder Pigments (hydrophobic treatment of silicon polymer) | 5.00 |
| Propylene Glycol | 2.00 |
| PPG-10 Cetyl Ether (Procetyl 10) | 7.00 |
| Diisopropyl Adipate* (Schercemol DIA) | 5.00 |
| PVP/Hexadecene Copolymer (Ganex V216) | 3.00 |
| Lanolin Fatty Acids (Amerdate LFA) | 3.00 |

*Can replace DIA w/Diisopropyl Dimerate

EXAMPLE VII

|  | % |
| --- | --- |
| Carboset XL-28 | 72.5 |
| Dry Powder Pigments | 2.5 |
| Glycerin | 0.5 |
| Laureth-4 (Brij 30) (PEG-4 Lauryl Ether) | 2.5 |
| Decaglycerol Decaoleate (Polyaldo DGDO) (Polyglyceryl-10 Decaoleate) | 2.5 |
| Polybutene (Indapol H-100) | 8.0 |
| PVP/Hexadecene Copolymer (Ganex V216) | 8.5 |
| Myristyl Propionate (Schercemol MP) | 3.0 |

EXAMPLE VIII

|  | % |
| --- | --- |
| Carboset XL-28 | 80.00 |
| Carboset 515 | 2.00 |
| H2O | 1.80 |
| NH4OH (28%) | 0.20 |
| Dry Powder | 4.00 |
| PEG-8 (carbowax 400) | 2.00 |
| Isopropyl Myristate | 5.00 |
| PVP/Eicosene Copolymer (Ganex V220) | 2.00 |

-continued

| | % |
|---|---|
| Polysorbate 81 (Tween 81) | 3.00 |

EXAMPLE IX

| | % |
|---|---|
| Carboset XL-28 | 77.95 |
| Dry Powder | 6.00 |
| Provol 50 (PPG-50 Dieyl Ether) | 2.00 |
| Lipocol SC-10 (Ceteareth-10) | 1.25 |
| Crodacol CS-50 (Cetearyl Alcohol) | 1.00 |
| PVP/Hexadecene Copolymer (Ganex V216) | 8.00 |
| Dioctyl Succinate (Wickenol 159) | 2.50 |
| Veegum *(5% disp in $H_2O$) | 1.00 |
| Xantham Gum* (Keltrol) | 0.25 |

*Can replace Veegum and Keltrol w/ CMC or other natural gum

EXAMPLE X

| | % |
|---|---|
| Carboset XL-28 | 43.00 |
| Carboset 525 | 4.50 |
| Carboset 515 | 2.00 |
| $H_2O$ | 40.25 |
| $NH_4OH$ (28%) | 0.60 |
| Dry Powder | 5.00 |
| Glycerin | 1.00 |
| PVP/Hexadecence Copolymer | 1.65 |
| Mineral Oil* | 1.30 |
| Glyconate SSE20 | 0.50 |
| Fragrance | 0.20 |
| Preservative | q.s. $H_2O$ |

*Can replace Mineral Oil w/Petrolatum

EXAMPLE XI

| | % |
|---|---|
| Carboset 525 | 10.20 |
| Carboset 515 | 2.00 |
| $H_2O$ | 75.75 |
| $NH_4OH$ (28%) | 1.25 |
| SDA40 Alcohol | 8.80 |
| Glycerin | 0.50 |
| PVP/Hexadecene Copolymer | 2.50 |
| Castor Oil | 0.70 |
| Capric/Caprylic Triglyceride | 1.00 |
| Fragrance | 0.30 |
| Preservative | q.s. $H_2O$ |

EXAMPLE XII

| | % |
|---|---|
| Carboset 525 | 10.20 |
| Carboset 515 | 2.00 |
| $H_2O$ | 75.05 |
| $NH_4OH$ (28%) | 1.25 |
| Dry Powder | 6.00 |
| Silica* (Cab-o-sil M5) | 0.50 |
| Glycerin | 0.50 |
| PVP/Hexadecene Copolymer | 2.20 |
| Castor Oil | 1.00 |
| Liponate PO4 (Pentaerythritol Tetraoleate) | 1.00 |
| Fragrance | 0.30 |
| Preservative | q.s. $H_2O$ |

*Can replace silica w/Carpobol (Carbomer 934)

EXAMPLE XIII

| | % |
|---|---|
| Carboset 525 | 10.20 |
| Carboset 515 | 2.00 |
| $H_2O$ | 74.55 |
| $NH_4OH$ (28%) | 1.25 |
| Dry Powder | 6.00 |
| Glycerin | 0.50 |
| PVP/Hexadecene Copolymer | 2.20 |
| Castor Oil | 1.25 |
| Cetearyl Alcohol* | 0.75 |
| Dipentaerythritol Hexacaprylate/Hexacaprate (Liponate DPC-6)** | 1.00 |
| Fragrance | 0.30 |
| Preservative | q.s. $H_2O$ |

*Can replace Cetearyl Alcohol w/ Oleyl Alcohol)
**Can replace DPC-6 w/ a Flexricin (esters of lower alcohols and ricinoleic acid)

EXAMPLE XIV

| | % |
|---|---|
| Carboset 525 | 10.20 |
| Carboset 515 | 2.00 |
| $H_2O$ | 75.31 |
| $NH_4OH$ | 1.25 |
| Simethicone (Antifoam AF Emulsion)* | 0.04 |
| Glycerin | 0.50 |
| Liponate DPC-6 | 1.25 |
| Ganex V216 | 2.20 |
| Castor Oil | 1.25 |
| Cetearyl Alcohol | 0.70 |
| Fragrance | 0.30 |
| Preservative | q.s. $H_2O$ |
| Dry Powder Pigments | 5.00 |

*Antifoam is added to Carboset 525 solv. before grinding pigments in

EXAMPLE XV

| | % |
|---|---|
| Dry Power Pigments | 7.00 |
| Carboset 525 | 5.40 |
| Carboset 515 | 12.50 |
| $H_2O$ | 51.55 |
| $NH_4OH$ | 1.75 |
| Simethicone | 0.05 |
| Magnasweet 110 | 0.20 |
| Glyceryl Trilaurate | 5.00 |
| Stearyl Alcohol | 0.75 |
| Steareth - 20 | 0.30 |
| Steareth - 10 | 0.45 |
| Stearyl heptanoate | 5.00 |
| PVP/hexadecene copolymer | 6.00 |
| Castor Oil | 4.0 |
| Fragrance | 0.05 |
| Preservative | q.s. $H_2O$ |

The lip-film formulations set forth above produce a liquid composition which is suitably applied to the lips using a brush or sponge applicator. It will be understood, however, that other applicator means can be used. In addition, salve like lip gloss or formed lip sticks could be made by increasing the amounts of oils and waxes present in a formulation.

The several examples set forth above are intended only to be illustrative. It will be understood that modifications in form and detail may be made within the scope of the following claims.

I claim:
1. A lip-film composition comprising:
(a) water;

(b) an alkali-dispersible, water-insoluble thermoplastic film-forming resin;
(c) a volatile base in sufficient quantity to solubilize the film-forming resin; and
(d) a water insoluble plasticizer, said lip-film composition forming a flexible, long-wearing, water-resistant film when applied to the lips and allowed to dry.

2. A lip-film composition according to claim 1, additionally comprising one or more cosmetically acceptable colorants.

3. A lip-film composition according to claim 1, wherein the film-forming resin is a copolymer comprising two or more monomers selected from the group consisting of acrylic acid, methacrylic acid, acrylamide, and esters of acrylic and methacrylic acid.

4. A lip-film composition according to claim 1, comprising 3 to 30% of the film-forming resin.

5. A lip-film composition according to claim 1, wherein the volatile base is ammonium hydroxide.

6. A lip-film according to claim 1, wherein the water insoluble plasticizer comprises one or more materials selected from the group consisting of simple esters of $C_3$–$C_{18}$ saturated acids with $C_3$–$C_{16}$ alcohols; simple esters of $C_{18}$ unsaturated acids with $C_3$–$C_{10}$ alcohols; diesters of $C_4$–$C_{36}$ saturated diacids with $C_3$–$C_{16}$ alcohols; glycerides of $C_{12}$–$C_{22}$ fatty acids; hydrocarbons; hydrocarbon polymers; polyvinylpyrrolidone/hydrocarbon copolymers; and fatty alcohol ethers of hydrocarbon polymers.

7. A lip-film composition according to claim 1, additionally comprising one or more materials selected from the group consisting of emollients, healing agents, medications and sunscreens.

* * * * *